United States Patent

Hilpert

[11] Patent Number: 5,965,733
[45] Date of Patent: Oct. 12, 1999

[54] PROCESS FOR MANUFACTURING AN αα'-DIAMINOALCOHOL

[75] Inventor: Hans Hilpert, Reinach, Switzerland

[73] Assignee: Hoffmann-La Roche Inc., Nutley, N.J.

[21] Appl. No.: 09/192,656

[22] Filed: Nov. 16, 1998

Related U.S. Application Data

[62] Division of application No. 09/112,651, Jul. 9, 1998, which is a division of application No. 08/900,413, Jul. 25, 1997, Pat. No. 5,847,144, which is a division of application No. 08/718,109, Sep. 18, 1996, Pat. No. 5,684,176, which is a division of application No. 08/514,329, Aug. 11, 1995, Pat. No. 5,591,885.

[30] Foreign Application Priority Data

Sep. 23, 1994 [CH] Switzerland ............... 2904/94
Dec. 9, 1994 [CH] Switzerland ............... 3736/94

[51] Int. Cl.⁶ .................................................. C07D 217/12
[52] U.S. Cl. ............................................................. 546/147
[58] Field of Search ................................................ 546/147

[56] References Cited

U.S. PATENT DOCUMENTS

| | | | |
|---|---|---|---|
| 5,157,041 | 10/1992 | Handa et al. ............... | 514/314 |
| 5,196,438 | 3/1993 | Martin et al. ............... | 514/311 |
| 5,430,041 | 7/1995 | Martin et al. ............... | 514/311 |
| 5,451,678 | 9/1995 | Parkes et al. ............... | 546/146 |
| 5,455,353 | 10/1995 | Hilpert ............................ | 546/146 |
| 5,502,210 | 3/1996 | Hilpert ............................ | 514/311 |

FOREIGN PATENT DOCUMENTS

| | | |
|---|---|---|
| 2 083 108 | 5/1993 | Canada . |
| 432 695 | 6/1991 | European Pat. Off. . |
| 525 880 | 2/1993 | European Pat. Off. . |
| 543 343 | 5/1993 | European Pat. Off. . |
| 635 493 | 1/1995 | European Pat. Off. . |
| 703 209 | 9/1995 | European Pat. Off. . |
| 94/11345 | 5/1994 | WIPO . |

OTHER PUBLICATIONS

Ghosh et al., J. Med. Chem., vol. 36, No. 2., pp. 292–294, Jan. 22, 1993.
Angrick, M. et al. Pharmezie i.u.Z., 13:83–88 (1984).
D'Aniello, F., J. Org. Chem., 54:5247–5250 (1992).
Konradi, A., et al., J. Am. Chem. Soc., 116:1316–1323 (1994).
Reetz, M., et al. Angew. Chem. Int. Ed., 30:1531–1546 (1991).
Shirahata, A., Tetrahedron Letters, 30(46):6393–6394 (1989).
Schilrin et al., Bioorganic & Medicinal Chemistry Letters 3(2):253–258 (1993).
Barluenga, J., et al., J. Chem. Soc., Chem Commun. 969–970 (1994).
Rich, D., et al., J. Med. Chem., 33:1258–1288 (1990).
Roush, W., et al., J. Org. Chem., 52:5127–5136 (1987).
Derwent Abstract No. 96–161587/17, 1996.

Primary Examiner—Zinna Northington Davis
Attorney, Agent, or Firm—George W. Johnston; William H. Epstein; John P. Parise

[57] ABSTRACT

A process for the manufacture of the α,α'-diaminoalcohol of formula

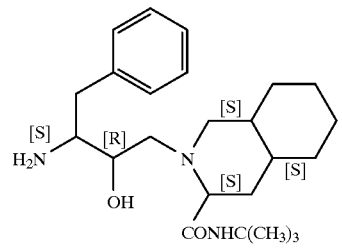

I is via N-protected L-phenylalanine lower alkyl esters, corresponding N-protected α-amino-α'-haloketones, and α-amino-α'-haloalcohols.

1 Claim, No Drawings

PROCESS FOR MANUFACTURING AN αα'-DIAMINOALCOHOL

CROSS REFERENCE TO RELATED APPLICATIONS

This is a continuation divisional of copending application (s) Ser. No. 09/112,651 filed on Jul. 9, 1998, which is a divisional of Ser. No. 08/900,413 filed on Jul. 25, 1997, now U.S. Pat. No. 5,847,144 which is a divisional of Ser. No. 08/718,109 filed on Sep. 18, 1996, now U.S. Pat. No. 5,684,176 which is a divisional of Ser. No. 08/514,329, filed Aug. 11, 1995, now U.S. Pat. No. 5,591,885.

BACKGROUND OF THE INVENTION

1. Field

The present invention is concerned with a novel process and intermediates for the manufacture of an α,α'-diaminoalcohol.

2. Description

The compound 2-[3(S)-amino-2(R)-hydroxy-4-phenylbutyl]-N-tert.butyl-decahydro-(4aS,8aS)-isoquinoline-3(S)-carboxamide of the formula

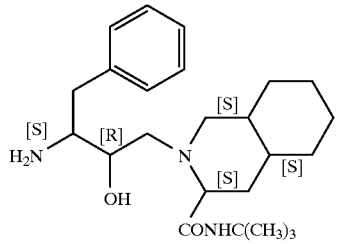

I is specifically described in Example 1 of European Patent Publication 0432695 and in corresponding U.S. Pat. No. 5,196,438, the contents of which are herein incorporated by reference, and is a valuable intermediate for the manufacture of the pharmacologically active compounds described in these patents. The compound of formula I can be converted as described in Examples 1 and 3 of the identified publications into pharmacologically active compounds suitable for treatment of viral infections, and especially infections caused by HIV and other retroviruses.

SUMMARY OF THE INVENTION

The present invention provides a process for the manufacture of 2-[3(S)-amino-2(R)-hydroxy-4-phenyl-butyl]-N-tert.butyl-decahydro-(4aS,8aS)-isoquinoline-3 (S)-carboxamide of the formula

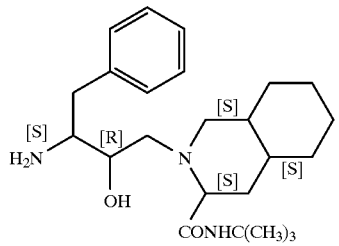

I and includes the novel intermediates generated therein.

The subject process comprises reacting an L-phenylalanine lower alkyl ester with a chloroformic acid ester of the formula ClCOOR$^1$, wherein R$^1$ is lower alkyl, benzyl, or phenyl, to produce a diester of formula

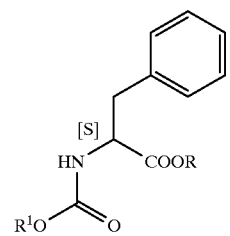

II wherein R is lower alkyl and R$^1$ is defined as above.

The resulting diester of the formula II is reacted with halogenated methyllithium to produce a halogenated α-aminoketone of formula

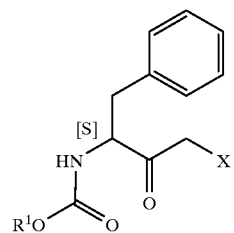

III wherein X is halogen and R$^1$ is defined as above.

The resulting halogenated a-aminoketone of formula III is then reduced to produce a halogenated α-amino catechol of formula

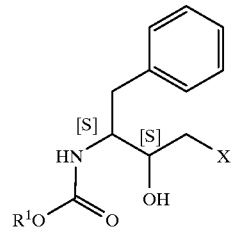

IV wherein X and R$^1$ are as defined above.

The resulting halogenated α-aminoalcohol of the formula IV is then cyclized with a base to produce an [(S)-1-[(S)-oxiran-2-yl]-2-phenyl-ethyl]-carbamic acid ester of formula

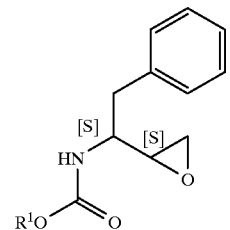

V wherein R$^1$ is as defined above.

The resulting [(S)- 1-[(S)-oxiran-2-yl]-2-phenyl-ethyl]-carbamic acid ester of formula V is then reacted with N-tert.butyl-decahydro-(4aS,8aS)-isoquinoline-3 (S)-carboxamide of formula

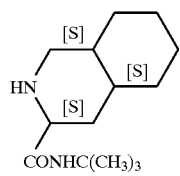

VI to produce a methyl (1S,2R)-[1-benzyl-3-[(3S,4aS,8aS)-3-tert-butoxycarbamoyl-octahydro-isoquinoline-2-yl]-2-hydroxy-propyl]-carbamate of formula

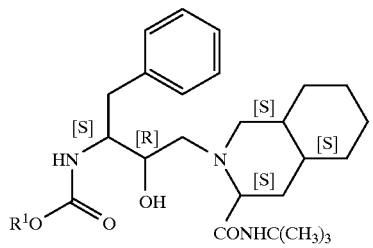

VII

The resulting methyl (1S,2R)-[1-benzyl-3-[(3S,4aS,8aS)-3-tert-butoxycarbamoyl-octahydro-isoquinoline-2-yl]-2-hydroxy-propyl]-carbamate of formula VII is then treated with a base to produce the 2-[3(S)-amino-2(R)-hydroxy-4-phenyl-butyl]-N-tert.butyl-decahydro-(4aS,8aS)-isoquinoline-3(S)-carboxamide of formula I.

DETAILED DESCRIPTION OF THE INVENTION

The invention will now be described in terms of its preferred embodiments. These embodiments are set forth to aid in understanding the invention, but are not to be construed as limiting.

The process in accordance with the invention comprises a) reacting a L-phenylalanine lower-alkyl ester with a chloroformic acid ester of the formula ClCOOR¹, wherein R¹ is lower alkyl, benzyl or phenyl, b) reacting a resulting diester of the formula

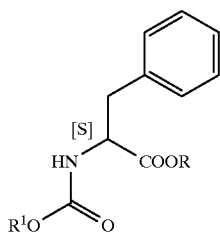

II wherein R is lower alkyl and R¹ has the above significance, with halogenated methyllithium, c) reducing a resulting halogenated α-aminoketone of the formula

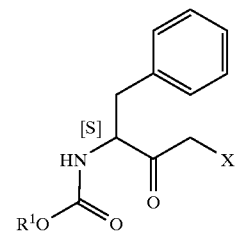

III wherein X is halogen and R¹ has the above significance, d) cyclizing a resulting halogenated α-aminoalcohol of the formula

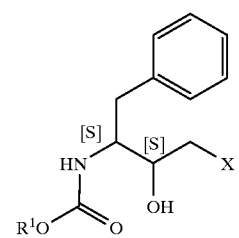

IV wherein X and R¹ have the above significance, with a base, e) reacting a resulting [(S)-1-[(S)-oxiran-2-yl]-2-phenyl-ethyl]-carbamic acid ester of the formula

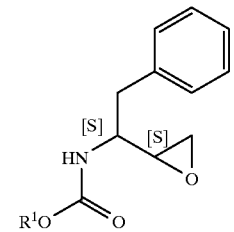

V wherein R¹ has the above significance, with N-tert.butyl-decahydro-(4aS,8aS)-isoquinoline-3(S)-carboxamide of the formula

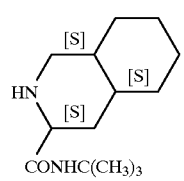

VI and f) treating the resulting methyl (1S,2R)-[1-benzyl-3-[(3S,4aS,8aS)-3-tert-butoxycarbamoyl-octahydro-isoquinoline-2-yl]-2-hydroxy-propyl]-carbamate of the formula

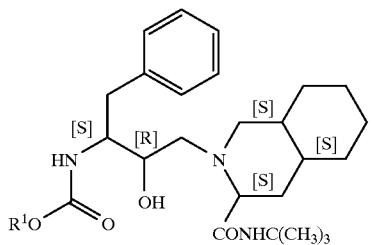

VII

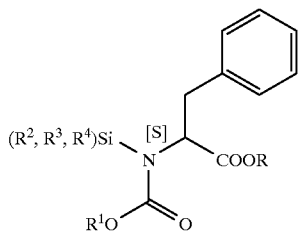

VIII

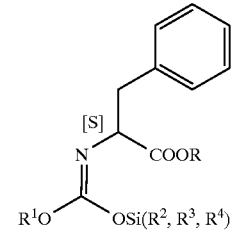

IX with a base.

The term "lower alkyl" used above refers to straight-chain or branched saturated hydrocarbon residues with 1–8, preferably 1–4, carbon atoms such as methyl, ethyl, n-propyl, isopropyl, n-butyl, isobutyl, sec.butyl, tert.butyl, pentyl, hexyl, heptyl, octyl, and the like. Halogen denotes bromine, chlorine, fluorine, or iodine.

The diesters of formula II are obtained according to known methods by heating L-phenylalanine with thionyl chloride in a lower alkanol such as methanol, evaporating the lower alkanol and reacting the resulting L-phenylalanine lower alkyl ester with a chloroformic acid ester $ClCOOR^1$, wherein $R^1$ signifies lower alkyl, for example, methyl or ethyl, benzyl, or phenyl, in a solvent such as a ketone, for example, methyl ethyl ketone, or an ether, for example, tert.butyl methyl ether, or a hydrocarbon, preferably toluene, in the presence of a base such as a lower alkylamine or an alkali or alkaline earth metal hydroxide, preferably potassium or sodium hydroxide, in the presence of water, at a temperature of 0°–60° C., preferably at 0°–10° C., at pH 4–10, preferably 6–7.

The halomethylation of the resulting diester II is preferably effected using halogenated methyllithium which is generated in situ. The latter is conveniently formed using dihalogenated methane, preferably using bromochloromethane, and a lower alkyl-lithium, preferably butyllithium or hexyllithium, in an ether, preferably tetrahydrofuran, at −20° to −120° C., preferably −80° C.

The halomethylation of the diester II to the halogenated α-aminoketone III can conveniently be carried out by a) reacting a diester of the formula

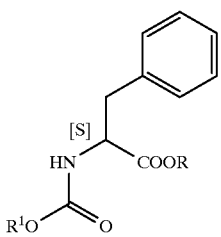

II wherein R is lower-alkyl and $R^1$ has the above significance, with a lower-alkyl-lithium and an organochlorosilane of the formula $ClSi(R^2,R^3,R^4)$, wherein $R^2$, $R^3$ and $R^4$ are lower alkyl or phenyl, and b) reacting a silyl-protected compound of formula VIII or IX formed as an intermediate wherein R, $R^1$, $R^2$, $R^3$ and $R^4$ have the above significance, in the presence of dihalogenated methane and a lower alkyl-lithium.

It has surprisingly been found that the foregoing protection of the carbamate group present in the diester II by a silyl group with the formation of the compounds of formula VIII or IX above as intermediates leads to a considerable increase in yield. Butyllithium or hexyllithium is preferably used as the lower alkyl-lithiurm and chlorotrimethylsilane is preferably used as the organochlorosilane $ClSi(R^2,R^3,R^4)$. Moreover, an almost complete conversion can be achieved using significantly less lower alkyl-lithium and dihalogenated methane.

The reduction of the halomethyl ketone III is conveniently carried out in a solvent such as toluene, tetrahydrofuran or an alcohol, preferably methanol, ethanol or isopropanol, at a temperature between −30 and 80° C., preferably −15° C. and 50° C., optionally under reduced pressure, using sodium bis(2-methoxyethoxy)aluminum hydride, lithium aluminum hydride, lithium aluminum tri-tert.-butoxyhydride, sodium borohydride, tetramethylammonium borohydride or, preferably, using an aluminum tri-alkoxide or lithium aluminum tri-alkoxyhydride. The term "alkoxide" embraces straight-chain or branched-chain saturated hydrocarbon oxides with 1–8, preferably 3–4, carbon atoms, namely methyl, ethyl, n-propyl, isopropyl, n-butyl, isobutyl, sec.-butyl and tert.-butyl oxide as well as pentyl, hexyl, heptyl and octyl oxides. The aluminum compounds can have identical or different alkoxide groups. Aluminum tri-isopropoxide and aluminum tri-sec.-butoxide are especially preferred compounds. The reagents lithium aluminum tri-tert.-butoxyhydride, aluminum tri-isopropoxide and aluminum tri-sec.-butoxide gave unexpectedly a high stereoselectivity of 95:5 of the (1S,2S) and (1S,2R) isomeric halohydrins IV, which could be crystallized from the reaction medium in >99% optical purity and with high yield.

The ring closure of the halohydrin of formula IV is conveniently carried out in a solvent such as ethanol or preferably a toluene/water mixture in the presence of a base such as an alkali or alkaline earth metal hydroxide, preferably sodium or potassium hydroxide, at a temperature between 0° and 80° C., preferably 40–50° C., whereby the epoxide of formula V which is formed need not be purified.

The reaction of the epoxide of formula V with the amide VI is conveniently carried out in a solvent such as a hydrocarbon, for example, toluene, or a lower alkanol, preferably ethanol, while heating to the reflux temperature, preferably at 20°–100° C., especially at 80° C.

The cleavage of the N-protecting group from the compound of formula VII is conveniently effected in a solvent such as water, ethanol or a mixture thereof using a base such as sodium or potassium hydroxide while heating to the reflux temperature, preferably at 20°–100° C., especially at 80°.

The compounds of formulas III and IV in which $R^1$ signifies methyl (namely formulas IIIa and IVa, respectively), especially methyl (S)-1-benzyl-3-chloro-2-oxopropyl)carbamate and, respectively, methyl (1 S,2S)-(1 -benzyl-3-chloro-2-hydroxypropyl) carbamate as well as the compounds of formulas V and VII in which $R^1$ signifies methyl (namely formulas Va and VIIa, respectively), namely methyl [(S)-1-[(S)-oxiran-2-yl]-2-phenethyl]carbamate and, respectively, methyl (1S,2R)-[1-benzyl-3-[(3S,4aS,8aS)-3-tert-butoxy carbamoyl-octahydro-isoquinolin-2-yl]-2-hydroxypropyl] carbamate, are novel and as such are encompassed by the present invention. The invention likewise embraces the compounds of formulas I, III and IV, which can be obtained by the process described above, as well as the use of the compounds of formulas III and IV for the manufacture of the compounds of formula I.

The compound of formula VI which is used as the starting material is known and corresponds to that of formula VII in European Patent Publication 0 432 695 and U.S. Pat. No. 5,196,438, the contents of which are herein incorporated by reference.

The following Examples are intended to illustrate the present invention, but are not limiting in any manner.

EXAMPLE 1

160 ml of thionyl chloride were added dropwise to 800 ml of methanol at 0° C. Subsequently, the mixture was treated with 330.4 g of L-phenylalanine and heated to 45° C. for 2.5 hours. The resulting solution was concentrated completely and the residue was taken up in 1.6 l of water and treated at 0° C. with 185 ml of methyl chloroformate while holding the pH between 6–7 with 40% sodium hydroxide solution. The solution was extracted with toluene, the extracts, after washing with water, were concentrated and the residue was dried at 45° C./0.1 mbar, there being obtained 474.6 g (100%) of pure methyl (S)-2-methoxycarbonylamino-3-phenyl-propionate. IR (KBr): 3338m (NH), 1726s br. (C=O), 1531s (amide II).

EXAMPLE 2

41.7 ml of a 2.6 molar solution of hexyllithium in hexane were added dropwise at –80° C. to a solution of 9.50 g of methyl (S)-2-methoxycarbonylamino-3-phenyl-propionate and 3.22 ml of bromochloromethane in 60 ml of tetrahydrofuran. Subsequently, a further 2.14 ml of bromochloromethane were added and the mixture was again treated with 23 ml of hexyllithium solution, a further 1.54 ml of bromochloromethane were added and the mixture was again treated with 7.7 ml of hexyllithium solution. The solution was treated at –80° C. with 15 ml of 20% methanolic hydrochloric acid, warmed to 22° and diluted with 100 ml of water and 40 ml of tetrahydrofuran. The phases were separated, the organic phase was washed with saturated sodium chloride solution, dried and concentrated. The residue was recrystallized from 40 ml of ethyl acetate and 160 ml of hexane and the crystallizate was dried, there being obtained 3.83 g (37%) of pure methyl (S)-(1-benzyl-3-chloro-2-oxo-propyl)-carbamate, m.p. 121°–122° C. IR (KBr): 3336s (NH), 1737s and 1686s (C=O), 1535s (amide II).

EXAMPLE 3

15.4 ml of a 2.6 molar solution of hexyllithium in hexane were added dropwise at –80° C. to a solution of 9.50 g of methyl (S)-2-methoxycarbonylamino-3-phenyl-propionate in 60 ml of tetrahydrofuran. Subsequently, the mixture was treated with 5.60 ml of chlorotrimethylsilane. The resulting suspension was stirred and treated with 3.22 ml of bromochloromethane. Subsequently, 18.4 ml of hexyllithium solution were added. The solution was treated at –80° C. with 11 ml of 20% methanolic hydrochloric acid, warmed to 22° and diluted with 100 ml of water and 40 ml of tetrahydrofuran. The phases were separated and the organic phase was washed with saturated sodium chloride solution, dried and concentrated. The residue was recrystallized from ethyl acetate and hexane and the crystallizate was dried, there being obtained 7.20 g (70%) of pure methyl (S)-(1-benzyl-3-chloro-2-oxo-propyl)-carbamate, m.p. 122°–123° C. IR (KBr): 3336s (NH), 1737s and 1686s (C=O), 1535s (amide II).

EXAMPLE 4

A) 33.06 g of lithium aluminum tri-tert.-butoxyhydride were added portionwise at 15° C. to a suspension of 25.57 g of methyl (S)-(1-benzyl-3-chloro-2-oxo-propyl)-carbamate in 280 ml of ethanol and the mixture was subsequently hydrolyzed at 0° C. with 140 ml of 3N hydrochloric acid and 170 ml of water. The suspension was concentrated to 370 ml, filtered and the residue was washed with water/ethanol (4:1) and dried, there being obtained 23.27 g (90%) of isomerically-pure methyl (1 S,2S)-(1 -benzyl-3-chloro-2-hydroxy-propyl)-carbamate, m.p. 163°–164.5° C. IR (KBr): 3323s, br. (NH, OH), 1689 (C=O), 1546s (amide II).

B) 25.57 g of methyl (S)-(1-benzyl-3-chloro-2-oxo-propyl)-carbamate were added portionwise at 22° C. to a suspension of 21.44 g of aluminum isopropoxide in 260 ml of isopropanol. The suspension was stirred at 50° C./400 mbar for 2 hours, hydrolyzed at 0° C. with 100 ml of 3N hydrochloric acid, subsequently concentrated to a volume of 125 ml, diluted with 125 ml of water, cooled to 0 ° C. and filtered. The residue was washed with water/isopropanol (4:1) and dried, there being obtained 13.01 g (89%) of isomerically-pure methyl (1S,2S)-(1 -benzyl-3-chloro-2-hydroxy-propyl)-carbamate, m.p. 162°–163.5° C. IR (KBr): 3323s, br. (NH, OH), 1689 (C=O), 1546s (amide II).

EXAMPLE 5

3.75 g of sodium borohydride were added portionwise at –15° C. to a suspension of 46.03 g of methyl (S)-(1-benzyl-3-chloro-2-oxo-propyl)-carbamate in 275 ml of methanol. The mixture was stirred for 1.5 hours, diluted with 21 ml of acetic acid and 460 ml of water, stirred at –15° C. for 1 hour and filtered. The residue was washed with water, recrystallized from 430 ml of isopropanol and the crystallizate was dried, there being obtained 28.68 g (62%) of a 98:2 mixture of the (1 S,2S):(1 S,2R)-isomers of methyl (1-benzyl-3-chloro-2-hydroxy-propyl)-carbamate, m.p. 161.5°–162.5° C. IR (KBr): 3323s, br. (NH, OH), 1689s (C=O), 1546s (amide II).

EXAMPLE 6

A mixture of 28.35 g of methyl (1S,2S)-(1-benzyl-3-chloro-2-hydroxy-propyl)-carbamate, 8.8 g of sodium hydroxide, 110 ml of toluene and 110 ml of water was stirred at 40° C. and the organic phase was then washed with water and concentrated. The residual methyl [(S)-1-[(S)-oxiran-2-yl]-2-phenyl-ethyl]-carbamate was taken up in 130 ml of ethanol, treated with 26.22 g of N-tert.butyl-decahydro-(4aS,8aS)-isoquinoline-3(S)-carboxamnide and heated at reflux for 5.3 hours. The suspension was diluted with 80 ml of water, cooled to 22° and filtered, and the residue was washed with a 1: 1 mixture of ethanol/water and dried, there being obtained 46.30 g (92%) of methyl (1S,2R)-[1-benzyl-3-[(3S,4aS,8aS)-3-tert-butoxycarbamoyl-octahydro-isoquinolin-2-yl]-2-hydroxy-propyl]-carbamate, m.p. 194°–195° C. IR (KBr): 341 lm and 3317m (NH, OH), 1715s and 1659s (C=O), 1548s (amide II).

EXAMPLE 7

A suspension of 41.37 g of methyl (1 S,2R)-[1 -benzyl-3-[(3 S,4aS,8aS)-3-tert-butoxycarbamoyl-octahydro-isoquinolin-2-yl]-2-hydroxy-propyl]-carbamate and 23.0 g of sodium hydroxide in 90 ml of ethanol and 90 ml of water was heated at reflux for 3.5 hours, diluted with 45 ml of water and cooled to 22°, and the separated solid was filtered off, washed with a 1:4 mixture of ethanol/water and dried, there being obtained 35.35 g (98%) of pure 2-[3(S)-amino-2(R)-hydroxy-4-phenyl-butyl]-N-tert.butyl-decahydro-(4aS,8aS)-isoquinoline-3(S)-carboxamide, m.p. 1730-1750C. IR (KBr):

3435m, br. (NH, OH), 1665s (C=O), 1562m (amide II).

Upon reading the present specification, various alternative embodiments will become obvious to the skilled artisan. These variations are to be considered within the scope and spirit of the present invention which is only to be limited by the claims which follow and their reasonable equivalents.

What is claimed is:

1. A compound of formula

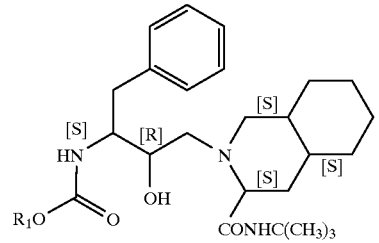

VIIa wherein $R^1$ is methyl.

* * * * *